United States Patent [19]

Malamas

[11] Patent Number: 5,444,086

[45] Date of Patent: Aug. 22, 1995

[54] NAPHTHALENYLMETHYL THIOPHENONES AS ANTIHYPERGLYCEMIC AGENTS

[75] Inventor: Michael S. Malamas, Jamison, Pa.

[73] Assignee: American Home Products Corporation, Madison, N.J.

[21] Appl. No.: 220,753

[22] Filed: Mar. 31, 1994

[51] Int. Cl.$^6$ .................. C07D 333/32; A61K 31/38
[52] U.S. Cl. ...................... 514/445; 549/62; 549/66
[58] Field of Search ............... 549/62, 66; 514/445

[56] References Cited

U.S. PATENT DOCUMENTS

| | | | |
|---|---|---|---|
| 4,283,348 | 8/1981 | Wheeler | 269/465 |
| 4,436,666 | 3/1984 | Wheeler | 260/455 |
| 4,665,174 | 5/1987 | Minai | 544/59 |
| 4,897,405 | 1/1990 | Alessi | 514/360 |
| 5,158,966 | 10/1992 | Lafferty et al. | 514/369 |

OTHER PUBLICATIONS

Tolstikov et al., Zh. Org. Khim., 27(1), 83–90 (CA 115:135732d) 1991 Abs. Only.
(CA 109:230684z) 1988 Abs. Only.
Stachel et al. "Regioselective α- and γ-Alkylation of Thiotetronic Acids", Arch. Pharm. vol., 321, 439–440, 1988.
CA 100:138813g (Tsuzuki et al. J. Antibiot., 36(11), 1589–91, 1983.

*Primary Examiner*—Glennon H. Hollrah
*Assistant Examiner*—Mary C. Cebulak
*Attorney, Agent, or Firm*—R. F. Boswell, Jr.

[57] ABSTRACT

This invention relates to benzyl and naphthalenylmethyl thiophenones and cyclopentenones, some of which are novel, which have oral antihyperglycemic activity in diabetic mice, a genetic animal model of non-insulin dependent diabetes mellitus. These compounds are represented by the formula

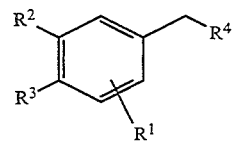

wherein:
R$^2$ and R$^3$ are independently selected from hydrogen, C$_{1-6}$ alkyl, halogen, C$_{1-6}$ alkoxy, thio-C$_{1-6}$ alkyl, or trifluoromethyl or R$^2$ together with R$^3$ forms a benzo ring fused to the phenyl ring and optionally substituted with one or two substituents independently selected from C$_{1-6}$ alkyl, halogen, C$_{1-6}$ alkoxy, thio-C$_{1-6}$ alkyl, or trifluoromethyl;
R$^1$ is selected from hydrogen, C$_{1-6}$ alkyl, halogen, C$_{1-6}$ alkoxy, thio-C$_{1-6}$ alkyl, or trifluoromethyl; and
R$^4$ is selected from the group consisting of:

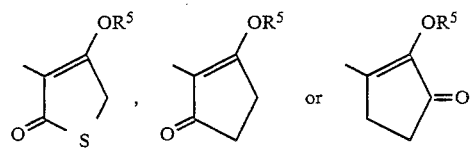

wherein R$^5$ is H or C$_{1-6}$ alkyl or a pharmaceutically acceptable salt thereof.

6 Claims, No Drawings

NAPHTHALENYLMETHYL THIOPHENONES AS ANTIHYPERGLYCEMIC AGENTS

FIELD OF INVENTION

This invention relates to benzyl and naphthalenylmethyl thiophenones and cyclopentenones as represented by formula I below, some of which are novel, which have demonstrated oral antihyperglycemic activity in diabetic mice, a genetic animal model of non-insulin-dependent diabetes mellitus (NIDDM or Type II). The formula I compounds or pharmaceutical compositions thereof are therefore useful in treating in treating hyperglycemia in mammals having non-insulin dependent diabetes mellitus.

BACKGROUND OF THE INVENTION

Diabetes mellitus is a syndrome characterized by abnormal insulin production, increased urinary output and elevated blood glucose levels. There are two major subclasses of diabetes mellitus. One is the insulin-dependent diabetes mellitus (IDDM or Type I), formerly referred to as juvenile onset diabetes since it was evident early in life, and noninsulin dependent diabetes mellitus (NIDDM or Type II), often referred to as maturity-onset diabetes. Exogenous insulin by injection is used clinically to control diabetes but suffers from several drawbacks. Insulin is a protein and thus cannot be taken orally due to digestion and degradation but must be injected. It is not always possible to attain good control of blood sugar levels by insulin administration. Insulin resistance sometimes occurs requiring much higher doses of insulin than normal. Another shortcoming of insulin is that while it may control hormonal abnormalities, it does not always prevent the occurrence of complications such as neuropathy, retinopathy, glomerulosclerosis, or cardiovascular disorders.

Orally effective antihyperglycemic agents are used to reduce blood glucose levels and to reduce damage to the nervous, retinal, renal or vascular systems through mechanisms affecting glucose metabolism. Such agents act in a variety of different mechanisms including inhibition of fatty acid oxidation, α-glycosidase inhibition, antagonism of $\alpha_2$-receptors and inhibition of gluconeogenesis. Two classes of compounds have predominated: the biguanides as represented by phenformin and the sulfonylureas as represented by tolbutamide (Orinase ®). A third class of compounds which has shown antihyperglycemic activity are thiazolidinediones of which ciglitazone is the prototype. Ciglitazone suppresses the symptoms of diabetes hyperglycemia, hyperttiglyceridemia and hyperinsulinemia [Diabetes 32, 804–10 (1983)].

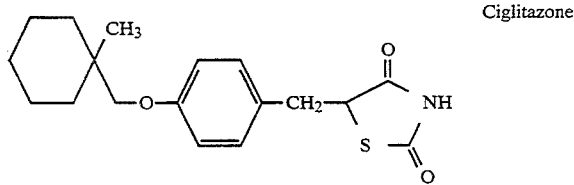

Ciglitazone

Still another class of antihyperglycemic agents are the N-arylalkyl-N-hydroxy ureas and the 2(arylalkyl)-[1,2,4-oxadiazolidine-3,5-diones. The published PCT patent application WO 92/03425 discloses compounds of the formula:

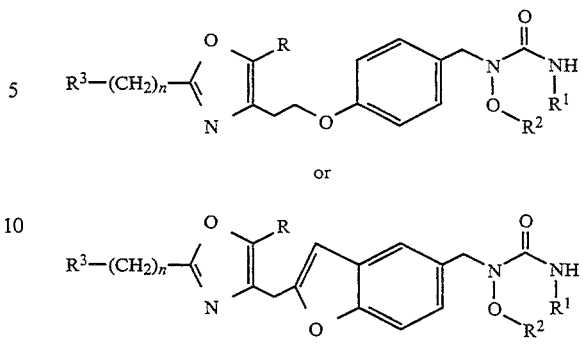

where $R^1$ and $R^2$ are independently H, $C_1$–$C_9$ alkyl, $C_3$–$C_7$ cycloalkyl, phenyl, etc. or $R^1$ and $R^2$ together are carbonyl, which have utility as hypoglycemic or hypocholesteremic agents.

The hypoglycemic properties of these compounds in ob/ob mice are discussed by Goldstein et al. J. Med. Chem. 36, 2238–2240 (1993).

SUMMARY OF THE INVENTION

The antihyperglycemic compounds of this invention useful in the method of treatment and pharmaceutical composition are represented by Formula I

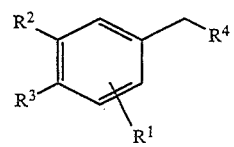

wherein:
$R^2$ and $R^3$ are independently selected from hydrogen, $C_{1-6}$ alkyl, halogen, $C_{1-6}$ alkoxy, thio-$C_{1-6}$ alkyl, or trifluoromethyl or $R^2$ together with $R^3$ forms a benzo ring fused to the phenyl ring and optionally substituted with one or two substituents independently selected from $C_{1-6}$ alkyl, halogen, $C_{1-6}$ alkoxy, thio-$C_{1-6}$ alkyl, or trifluoromethyl;
$R^1$ is selected from hydrogen, $C_{1-6}$ alkyl, halogen, $C_{1-6}$ alkoxy, thio-$C_{1-6}$ alkyl, or trifluoromethyl;
and
$R^4$ is selected from the group consisting of:

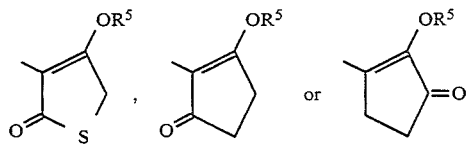

wherein $R^5$ is H or $C_{1-6}$ alkyl, and the pharmaceutically acceptable salts thereof that can be formed when $R^5$ is hydrogen.

The novel compounds of this invention are those of Formula Ia

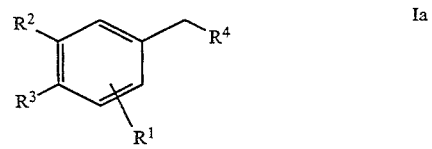

wherein:

R² and R³ are independently selected from hydrogen, $C_{1-6}$ alkyl, halogen, $C_{1-6}$ alkoxy, thio-$C_{1-6}$ alkyl, or trifluoromethyl or R² together with R³ forms a benzo ring fused to the phenyl ring and optionally substituted with one or two substituents independently selected from $C_{1-6}$ alkyl, halogen, $C_{1-6}$ alkoxy, thio-$C_{1-6}$ alkyl, or trifluoromethyl;

R¹ is selected from hydrogen, $C_{1-6}$ alkyl, halogen, $C_{1-6}$ alkoxy, thio-$C_{1-6}$ alkyl, or trifluoromethyl; and R⁴ is selected from the group consisting of:

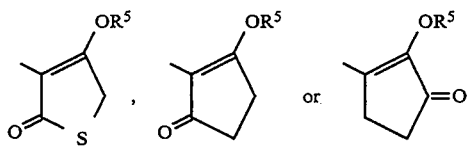

wherein R⁵ is H or $C_{1-6}$ alkyl, and the pharmaceutically acceptable salts thereof that can be formed when R⁵ is hydrogen, with a proviso that when R⁴ is

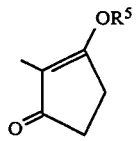

and R² and R³ do not form a benzo ring fused to the phenyl ring, then at least one of R¹, R², or R³ must be other than hydrogen.

In the terms used above, $C_{1-6}$ alkyl means a straight or branched chain hydrocarbon having from one to six carbons such as methyl, ethyl, isopropyl, propyl, butyl, isobutyl, pentyl, neopentyl or hexyl. The term halogen means fluorine, chlorine, bromine or iodine. The term $C_{1-6}$ alkoxy means an —O—$C_{1-6}$ alkyl group and the term thio-$C_{1-6}$ alkyl means —S— $C_{1-6}$ alkyl. The term "R² together with R³ forms a benzo ring fused to the phenyl ring and optionally substituted with one or two substituents independently selected from $C_{1-6}$ alkyl, halogen, $C_{1-6}$ alkoxy, thio-$C_{1-6}$ alkyl, or trifluoromethyl" means a naphthalenyl ring of formula II below wherein X¹ and X² are selected from $C_{1-6}$ alkyl, halogen, $C_{1-6}$ alkoxy, thio-$C_{1-6}$ alkyl, or trifluoromethyl.

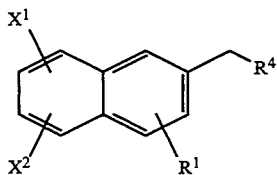

II

The term "pharmaceutically acceptable salt" means cationic addition salts formed between an invention compound wherein R⁵ is hydrogen and an alkali metal or alkaline earth metal such as sodium, potassium or calcium.

It should also be recognized that the compounds of this invention when isolated as solids may be hydrated or solvated and are considered pharmaceutically equivalent.

In the above formulas I, Ia, or II, it will be apparent to those skilled in the art that the group R⁴ may exist in a tautomeric diketo form when R⁵ is hydrogen.

The most preferred compounds of the present invention are set forth below:

4-hydroxy-3-[[4-(methylthio)phenyl]methyl]-2(5H)-thiophenone, 4-hydroxy-3-(2-naphthalenylmethyl)-2(5H)-thiophenone, 3-[(4-bromophenyl)methyl]-4-hydroxy-2(5H)-thiophenone, 4-hydroxy-3-[[4-(2-phenylethoxy)phenyl]methyl]-2(5H)-thiophenone, 3-(1-bromo-naphthalen-2-ylmethyl )-4-hydroxy-2(5H)-thiophenone, 3-[(3,4-dichlorophenyl)methyl]-4-hydroxy-2(5H)-thiophenone, 3-hydroxy-2(2-naphthalenylmethyl)-2-cyclopenten-1-one, 3-methoxy-2(2-naphthalenylmethyl)-2-cyclopenten-1-one, 2-hydroxy-3-(2-naphthalenylmethyl)-2-cyclopenten-1-one, 3-(4-bromo-benzyl)-2-hydroxy-2-cyclopenten-1-one, and 3-hydroxy-2-[(1-methyl-2-naphthalenyl)methyl]-2-cyclopenten-1-one.

DETAILED DESCRIPTION OF THE INVENTION

The benzyl and naphthalenylmethyl thiophenones and cyclopentenones of the present invention were prepared according to the following synthetic schemes. The cyclopentanones and thiophenones used in the syntheses are commercially available. The benzyl or naphthalenylmethyl bromides or chlorides are either commercially available or readily prepared according to published procedures.

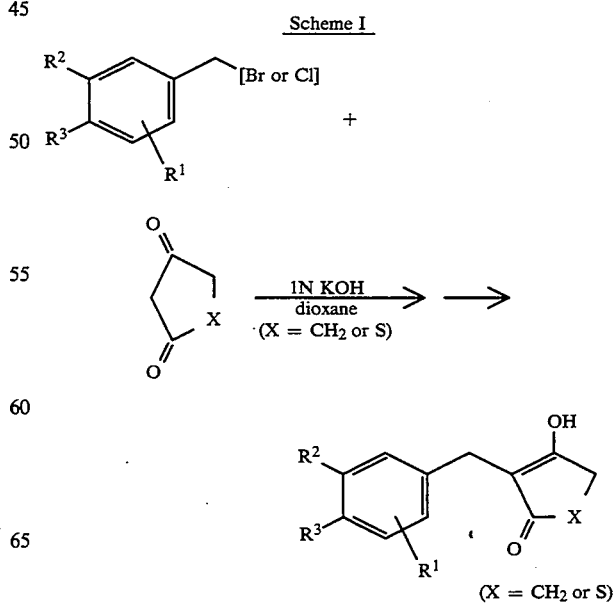

Scheme II

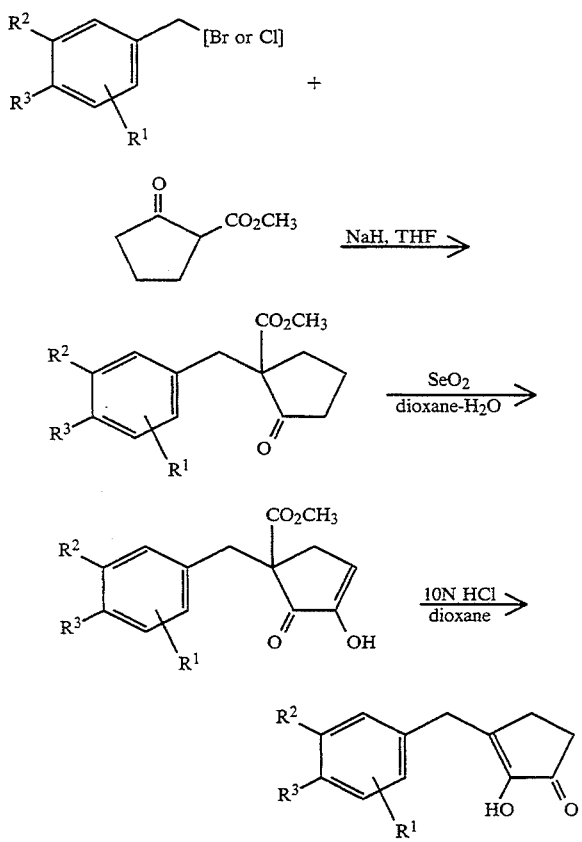

The following specific examples show the methods of preparation of the above reaction schemes and are included for illustrative purposes only. Still other methods of preparation may be apparent to those skilled in the art. The starting materials, reagents, and intermediates are either commercially available or can be prepared by standard literature procedures.

EXAMPLE 1

4-Hydroxy-3-[[4-(methylthio)phenyl]methyl]-2(5H)-thiophenone

To a suspension of 4-methylthiobenzyl bromide (5.6 g. 25.8 mmol), thiotetronic acid (3.0 g, 25.8 mmol) in dioxane (50 ml), was added aqueous potassium hydroxide (25.8 mL). The mixture was stirred at temperatures in the range of 65°–70° C. for 3 hours. Then, the mixture was cooled to room temperature, poured into H$_2$O, acidified with HCl (2N) and extracted with EtOAc. The organic extracts were dried over MgSO$_4$. Evaporation and purification by flash chromatography on acid washed (5% H$_3$PO$_4$ in MeOH) silica gel (eluting solvent hexane/EtOAc ⅓) gave a white solid (1.72 g, 26.5%): m.p. 206°–208° C.

Analysis for: C$_{12}$H$_{12}$O$_2$S$_2$ Calcd: C, 57.11; H, 4.79
Found: C, 57.39; H, 4.84

EXAMPLE 2

4-Hydroxy-3-(2-nanhthalenylmethyl)-2(5H)-thiophenone

The title compound was prepared in substantially the same manner as described in example 1, and was obtained as a white solid, m.p. 238°–239° C.

Analysis for: C$_{15}$H$_{12}$O$_2$S Calc'd: C, 70.29; H, 4.72
Found: C, 70.21; H, 4.62

EXAMPLE 3

3-[(4-Bromophenyl)methyl]-4-hydroxy-2(5H)-thiophenone

The title compound was prepared in substantially the same manner as described in example 1, and was obtained as a white solid, m.p. 201°–202° C.

Analysis for: C$_{11}$H$_9$BrO$_2$S Calc'd: C, 46.33; H, 3.18
Found: C, 46.60; H, 3.41

EXAMPLE 4

4-Hydroxy-3-[4-(2-phenylethoxy)phenyl]methyl]-2(5H)-thiophenone

The title compound was prepared in substantially the same manner as described in example 1, and was obtained as a white solid, m.p. 170°–171° C.

Analysis for: C$_{19}$H$_{18}$O$_3$S Calc'd: C, 69.91; H, 5.56
Found: C, 69.59; H, 5.72

EXAMPLE 5

3-(1-Bromo-naphthalen-2-ylmethyl)-4-hydroxy-2(5H)-thiophenone

The title compound was prepared in substantially the same manner as described in example 1, and was obtained as a white solid, m.p. 205°–206° C.

Analysis for: C$_{15}$H$_{11}$BrO$_2$S Calc'd: C, 53.74; H, 3.31
Found: C, 53.34; H, 3.24

EXAMPLE 6

3-[(3,4-Dichlorophenyl)methyl]4-hydroxy-2(5H)-thiophenone

The title compound was prepared in substantially the same manner as described in example 1, and was obtained as a white solid, m.p. 239°–240° C.

Analysis for: C$_{11}$H$_8$O$_2$S Calc'd: C, 48.02; H, 2.93
Found: C, 48.05; H, 2.98

EXAMPLE 7

3-Hydroxy-2(2-naphthalenylmethyl)-2-cyclopenten-1-one

The title compound was prepared in substantially the same manner as described in example 1.

1,3-Cyclopentanedione was used in place of thiotetronic acid. The title compound was obtained as a white solid, m.p. 230°–231 ° C.

Analysis for: C$_{16}$H$_{14}$O$_2$ Calc'd: C, 80.65; H, 5.92
Found: C, 80.25; H, 6.12

EXAMPLE 8

3-Methoxy-2(2-naphthalenylmethyl)-2-cyclopenten-1-one

A mixture of 2-hydroxy-2(2-naphthalenylmethyl)-2-cyclopenten-1-one (1.1 g, 4.62 mmol), dimethylsulfate (0.66 ml, 6.93 mmol), potassium carbonate (0.96 g, 6.93 mmol) and acetone (20 ml) was refluxed for 2 hours. The mixture was then poured into H$_2$O and extracted with EtOAc. The organic extracts were dried over MgSO$_4$. Evaporation and crystallization from ether/hexane (after cooling to −20° C.) gave a white solid (0.78 g, 67%): m.p. 70°–71° C.

Analysis for: C$_{17}$H$_{16}$O$_2$ Calc'd: C, 80.93; H, 6.39
Found: C, 80.53; H, 6.49

EXAMPLE 9

2-Hydroxy-3-(2-naphthalenylmethyl)-2-cyclopenten-1-one

Step a) To a cold (0° C.) solution of 2-(carbomethoxy)cyclopentanone (4.37 ml, 35.21 mmol) in THF (100 ml) was added sodium hydride (80% dispersion in mineral oil, 1.06 g, 35.21 mmol) portionwise. After stirring for 30 minutes, 2-(bromomethyl)naphthalene (7.78 g, 35.21 mmol) in THF (10 ml) was added and the reaction mixture was allowed to come to room temperature. The mixture was stirred for 20 hours, poured into $H_2O$, acidified with HCl (2N) and extracted with EtOAc. The organic extracts were dried over $MgSO_4$. Evaporation gave an oil (8.4 g) which was taken in dioxane (100 ml)/$H_2O$ (10 ml) and treated with selenium dioxide (3.3 g, 29.78 mmol). The mixture was stirred at 100° C. for 6 hours, poured into $H_2O$ and extracted with EtOAc. Evaporation and purification by flash chromatography on silica gel (eluting solvent hexane/EtOAc 3/1) gave a yellow solid (3.5 g): m.p. 92°–94° C.

$^1$H NMR (DMSO-$d_6$) δ 2.5–2.85 (m, 2H, —$CH_2$—), 3.31 (s, 2H, —$CH_2$—). 3.68 (s, 3H, $CO_2CH_3$), 6.35 (t, J=4.5 Hz, 1H, CH), 7.25 (s, d, J=7.5 Hz, 1H, Ar—H), 7.5 (m, 2H, Ar—H), 7.7 (s, 1H, Ar—H), 7.8–8.0 (m, 3H, Ar—H), 9.62 (s, 1H, —OH).

Step b) A mixture of 3-hydroxy-1-naphthalen-2-ylmethyl-2-oxo-cyclopent-3-enecarboxylic acid methyl ester (3.0 g, 10.71 mmol), dioxane (50 ml), and HCl (10N, 50 ml) was stirred at 100° C. for 5 hours. The mixture was cooled to room temperature, poured into $H_2O$ and extracted with EtOAc. The organic extracts were dried over $MgSO_4$. Evaporation and crystallization from acetone/ether gave a brown solid (1.75 g, 69%): m.p. 120°–122° C.

Analysis for: $C_{15}H_{14}O_2$ Calc'd: C, 80.65; H, 5.92 Found: C, 80.70; H, 5.93

EXAMPLE 10

3-(4-Bromophenylmethyl)-2-hydroxy-2-cyclopenten-1-one

The title compound was prepared in substantially the same manner as described in example 9, steps a–b, and was obtained as a white solid, m.p. 144°–145° C.

Analysis for: $C_{12}H_{11}BrO_2$ Calc'd: C, 53.95; H, 4.15 Found: C, 53.98; H, 4.09

EXAMPLE 11

3-hydroxy-2-[(1-methyl-2-naphthalenyl)methyl]-2-cyclopenten-1-one

The title compound was prepared in substantially the same manner as described in example 7, and was obtained as a white solid, m.p. 226°–228° C.

Analysis for: $C_{17}H_{16}O_2$ Calc'd: C, 80.93; H, 6.39 Found: C, 80.55; H, 6.65

PHARMACOLOGY

The diabetic db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia (1). Furthermore, the db/db mouse will eventually develop some of the long-term complications that have been associated with diabetes mellitus (1). In spite of these commonalities, the acute administration of sulfonylureas (even at extremely high doses) will not reduce the hyperglycemia of the db/db mouse (2). The ability of a few other hypoglycemic agents to be effective in this species suggest that the other agents have mechanism of action which are different from that of the sulfonylureas (2,3,4,5). Such compounds, therefore, are more likely to be efficacious in the population of type II diabetic patients that do not respond to sulfonylurea therapy.

Determination of Blood Glucose Lowering in db/db Mice

On the morning of Day 1, 35 mice [male diabetic db/db (C57BL/KsJ) mice (Jackson Laboratories), 2–7 months of age and 50–70 g] were fasted for 4 hours, weighed and a baseline blood sample (15–30 µl) was collected from the tail-tip of each mouse without anesthesia, and placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels (N=6 for vehicle and N=4 for each drug group). On the afternoon of Days 1, 2 and 3, the vehicle, control or test drugs were administered (p.o.) to the ad libitum fed mice. On the morning of Day 4, the mice were weighed and food removed, but water was available ad libitum. Three hours later, a blood sample was collected and then the mice were given the fourth administration of drug or vehicle. Blood samples were collected again from the unanesthetized mice at 2 and 4 hours after drug administration. The plasma was separated and levels of glucose in plasma was determined by the Abbott VP Analyzer.

For each mouse, the percent change of its plasma glucose level on Day 4 (mean of the 2 and 4 hr samples) from respective level before drug administration (Day 1 baseline sample) is determined as follows:

$$\frac{\text{mean of 2 and 4 hr samples (Day 4)}}{\text{Baseline Sample (Day 1)}} \times 100$$

Analysis of variance followed by Dunnett's multiple comparison (one-sided) will be used to estimate the degree of statistical significance of the difference between the vehicle control group and the individual drug-treated groups. A drug will be considered active, at the specific dosage administered, if the difference of the plasma glucose level has a $p<0.05$. The actual difference between the mean percent change of the vehicle and drug-treated groups is shown in Table 1.

The positive control, ciglitazone produces a 18 to 34% (26% average) decrease in plasma glucose levels at 100 mg/kg/day×4 days, p.o. The compounds of examples 1–11 are comparable with the results for ciglitazone as shown in Table I.

TABLE 1

| Compound of Example No. | Dose mg/kg, p.o. | % Change glucose |
| --- | --- | --- |
| 1 | 100 | −47 |
| 2 | 100 | −49 |
| 3 | 100 | −38 |
| 4 | 100 | −35 |
| 5 | 100 | −24 |
| 6 | 100 | −19 |
| 7 | 100 | −27 |

TABLE 1-continued

| Compound of Example No. | Dose mg/kg, p.o. | % Change glucose |
|---|---|---|
| 8 | 100 | −27 |
| 9 | 100 | −31 |
| 10 | 100 | −18 |
| 11 | 100 | −21 |
| ciglitazone | 100 | −26 |

1. Coleman, D. L. (1982) Diabetes-obesity syndromes in mice. Diabetes 31 (Suppl. 1); 1–6.
2. Tutwiler, G. F., T. Kirsch, and G. Bridi (1978). A pharmacologic profile of McN-3495 [N-(1-methyl-2-pyrrolidinylidene)-N'-phenyl-1-pyrrolidine-carboximidamide], a new, orally effective hypoglycemic agent. Diabetes 27:856–857.
3. Lee, S. M., G. Tutwiler, R. Bressler, and C. H. Kircher (1982). Metabolic control and prevention of nephropathy by 2-tetradecylglycidate in the diabetic mouse (db/db). Diabetes 31:12–18.
4. Chang, A. Y., B. W. Wyse, B. J. Gilchrist, T. Peterson, and R. Diani (1983) Ciglitazone, a new hypoglycemic agent. 1.Studies in ob/ob and db/db mice, diabetic Chinese hamsters, and normal and streptozocin-diabetic rats. Diabetes 32: 830–838.
5. Hosokawa, T., K. Ando, and G. Tamura (1985). An ascochlorin derivative, AS-6, reduces insulin resistance in the genetically obese diabetic mouse, db/db. Diabetes 34: 267–274.

Pharmaceutical Composition

Based on the results of the pharmacological assay, the compounds of this invention are useful in the treatment of hyperglycemia in diabetes mellitus.

The compounds may be administered neat or with a pharmaceutical carder to a mammal in need thereof. The pharmaceutical carder may be solid or liquid and the active compound shall be a therapeutically effective amount.

A solid carder can include one or more substances which may also act as flavoring agents, lubricants, solubilizers, suspending agents, fillers, glidants, compression aids, binders or tablet-disintegrating agents; it can also be an encapsulating material. In powders, the carder is a finely divided solid which is in admixture with the finely divided active ingredient. In tablets, the active ingredient is mixed with a carder having the necessary compression properties in suitable proportions and compacted, in the shape and size desired. The powders and tablets preferably contain up to 99% of the active ingredient. Suitable solid carders include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carders are used in preparing solutions, suspensions, emulsions, syrups, elixirs and pressurized compositions. The active ingredient can be dissolved or suspended in a pharmaceutically acceptable liquid carder such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carders for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g fractionated coconut oil and arachis oil). For parenteral administration, the carder can also be an oily ester such as ethyl oleate and isopropyl myristate. Sterile liquid carders are useful in sterile liquid form compositions for parenteral administration. The liquid carder for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. A dosage range of from 0.1 to 200 mg/kg/day is contemplated, with a preferred dosage of from 0.1 to 100 mg/kg/day. Due to uncertainty in relating laboratory mouse study data to other mammals, the degree of hyperglycemia, and the compound selected, the dosages used in the treatment of non-insulin dependent diabetes mellitus must be subjectively determined by a physician or veterinarian according to standard medical or veterinary practice.

What is claimed is:

1. A compound according to the formula

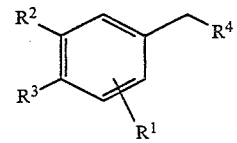

wherein:
$R^2$ together with $R^3$ forms a benzo ring fused to the phenyl ring and optionally substituted with one or two substituents independently selected from $C_{1-6}$ alkyl, halogen, $C_{1-6}$ alkoxy, thio-$C_{1-6}$ alkyl, or trifluoromethyl;
$R^1$ is selected from hydrogen, $C_{1-6}$ alkyl, halogen, $C_{1-6}$ alkoxy, thio-$C_{1-6}$ alkyl, or trifluoromethyl; and
$R^4$ is:

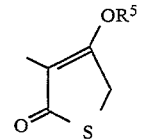

wherein $R^5$ is H or $C_{1-6}$ alkyl, or a pharmaceutically acceptable salt thereof.

2. A method of treating hyperglycemia in a mammal which comprises administration thereto of a therapeutically effective amount of a compound having the formula

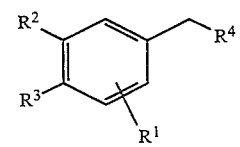

wherein:

R² together with R³ forms a benzo ring fused to the phenyl ring and optionally substituted with one or two substituents independently selected from $C_{1-6}$ alkyl, halogen, $C_{1-6}$ alkoxy, thio-$C_{1-6}$ alkyl, or trifluoromethyl;

R¹ is selected from hydrogen, $C_{1-6}$ alkyl, halogen, $C_{1-6}$ alkoxy, thio-$C_{1-6}$ alkyl, or trifluoromethyl; and R⁴ is:

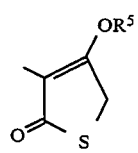

wherein R⁵ is H or $C_{1-6}$ alkyl; or a pharmaceutically acceptable salt thereof.

3. A method of treatment according to claim 2 wherein the therapeutically effective compound used is selected from the group consisting of:

4-hydroxy-3-(2-naphthalenylmethyl)-2(5H)-thiophenone, 3-(1-bromo-naphthalen-2-ylmethyl)-4-hydroxy-2(5H)-thiophenone, and 4. A pharmaceutical composition which comprises a pharmaceutically acceptable carrier and a therapeutically effective amount of a compound of the formula

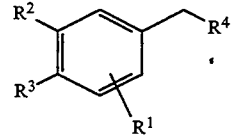

wherein:

R² together with R³ forms a benzo ring fused to the phenyl ring and optionally substituted with one or two substituents independently selected from $C_{1-6}$ alkyl, halogen, $C_{1-6}$ alkoxy, thio-$C_{1-6}$ alkyl, or trifluoromethyl;

R¹ is selected from hydrogen, $C_{1-6}$ alkyl, halogen, $C_{1-6}$ alkoxy, thio-$C_{1-6}$ alkyl, or trifluoromethyl; and R⁴ is:

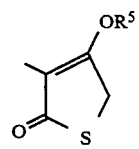

wherein R⁵ is H or $C_{1-6}$ alkyl, or a pharmaceutically acceptable salt thereof.

5. A compound according to claim 1 which is 4-hydroxy-3-(2-naphthalenylmethyl)-2(5H)-thiophenone.

6. A compound according to claim 1 which is 3-(1-bromo-naphthalen-2-ylmethyl)-4-hydroxy-2(5H)-thiophenone.

* * * * *